United States Patent
Kwasnik et al.

[11] Patent Number: 6,083,003
[45] Date of Patent: Jul. 4, 2000

[54] ELECTROMAGNETICALLY ACTUATED VALVE FOR HYDRAULIC MOTOR VEHICLE BRAKE SYSTEMS

[76] Inventors: Robert J. Kwasnik; Michael W. Kwasnik, Jr., both of 108 Woodrow Ave., Chattanooga, Tenn. 37415-2821; Hal K. Bowling, 430 Chestnut St., Suite 202, Chattanooga, Tenn. 37409; Claude E. Smith, 108 Woodrow Ave., Chattanooga, Tenn. 37415-2821

[21] Appl. No.: 09/177,936

[22] Filed: Oct. 23, 1998

[51] Int. Cl.[7] ................................................ A61C 17/06
[52] U.S. Cl. ............................................ 433/91; 606/161
[58] Field of Search ................................ 433/91, 92, 95, 433/96, 142, 143; 606/161

[56] References Cited

U.S. PATENT DOCUMENTS

| | | |
|---|---|---|
| 148,290 | 3/1874 | Fisk . |
| D. 292,825 | 11/1987 | Dragen ...................... D24/16 |
| D. 306,905 | 3/1990 | Barclay ...................... D22/16 |
| D. 338,063 | 8/1993 | Idowu ...................... D24/115 |
| 1,728,956 | 9/1929 | Darmitzel . |
| 2,274,893 | 3/1942 | Freedman ...................... 32/33 |
| 2,405,029 | 7/1946 | Gallanty et al. ...................... 606/161 |
| 2,638,670 | 5/1953 | Wyne ...................... 433/95 |
| 2,715,899 | 5/1955 | MacLean ...................... 433/142 |
| 3,520,300 | 7/1970 | Flower, Jr. ...................... 128/276 |
| 3,593,707 | 7/1971 | Pifer ...................... 128/56 |
| 3,768,477 | 10/1973 | Anders et al. ...................... 433/91 |
| 3,973,558 | 8/1976 | Stouffer et al. ...................... 128/66 |
| 4,058,896 | 11/1977 | Moore ...................... 32/33 |
| 4,265,621 | 5/1981 | McVey ...................... 433/91 |
| 4,538,631 | 9/1985 | Prance ...................... 132/84 |
| 4,672,953 | 6/1987 | DiVito ...................... 128/66 |
| 4,808,109 | 2/1989 | Thornton ...................... 433/216 |
| 4,900,316 | 2/1990 | Yamamoto ...................... 604/313 |
| 5,123,840 | 6/1992 | Nates ...................... 433/95 |
| 5,151,094 | 9/1992 | Hanifl ...................... 433/91 |
| 5,226,197 | 7/1993 | Nack et al. ...................... 606/161 |
| 5,441,410 | 8/1995 | Segerdal ...................... 433/93 |
| 5,463,792 | 11/1995 | Hogan et al. ...................... 15/322 |
| 5,779,654 | 7/1998 | Foley et al. ...................... 606/161 |

*Primary Examiner*—Todd E. Manahan
*Attorney, Agent, or Firm*—Miller & Martin, LLP

[57] ABSTRACT

An oral vacuum and scraper device is disclosed for removing foreign matter such as mouth rinse, toothpaste, food particles, volatile sulfur compound producing bacteria, and the like from a mouth. The vacuum device, in a preferred embodiment, utilizes a venturi device to create suction when fluid flows through the venturi device. A mouthpiece has a suction area located near an edge of the head of the mouthpiece and incorporates either, or both of, a scraper and bristles.

19 Claims, 4 Drawing Sheets

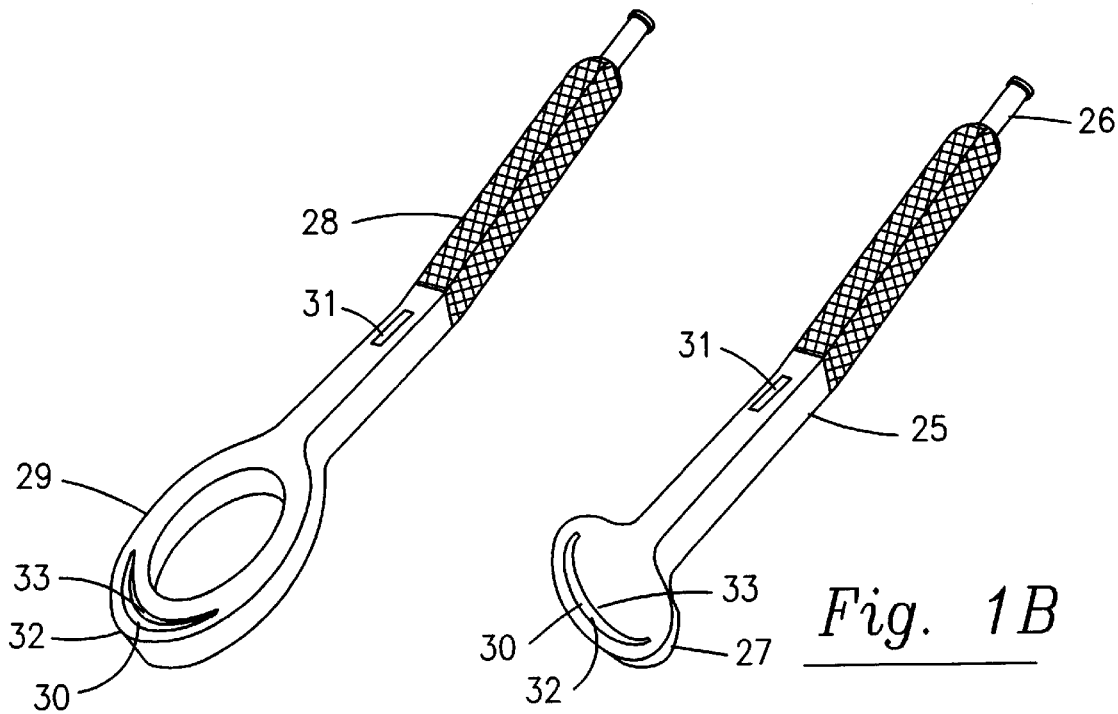
Fig. 1A
Fig. 1B
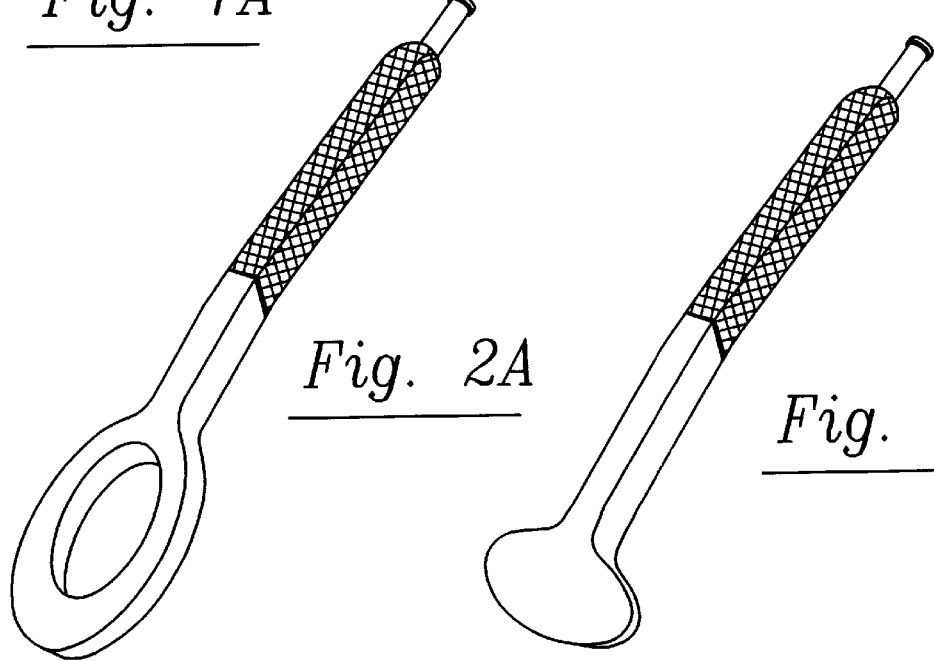
Fig. 2A
Fig. 2B

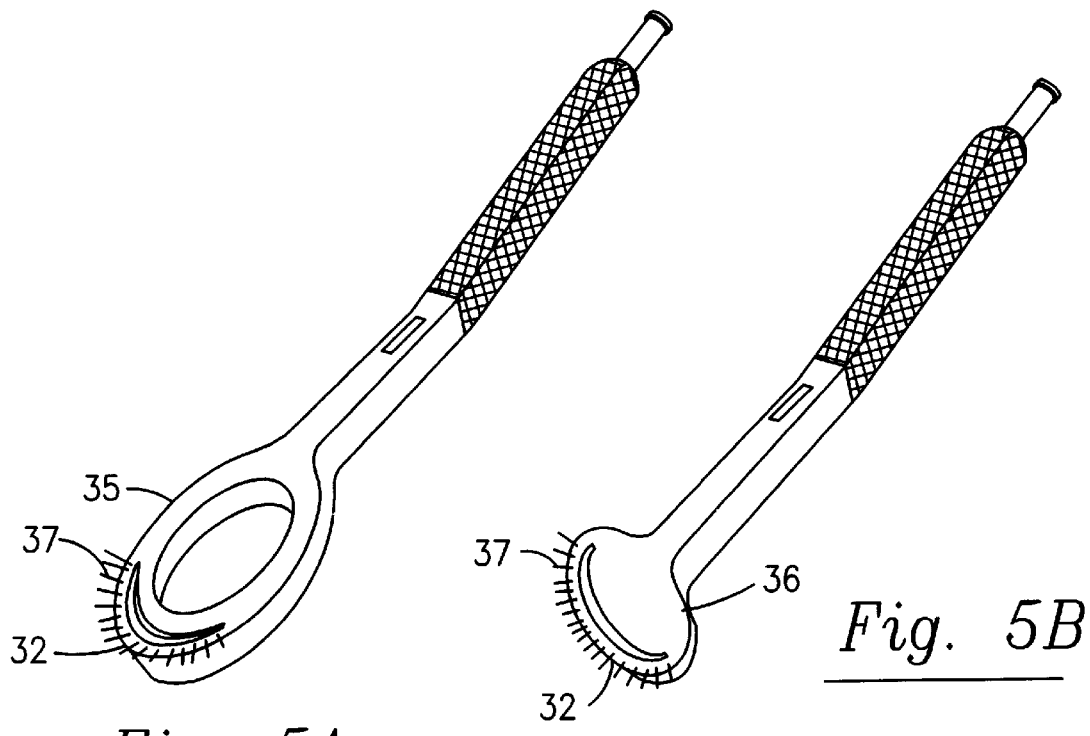
Fig. 5A
Fig. 5B
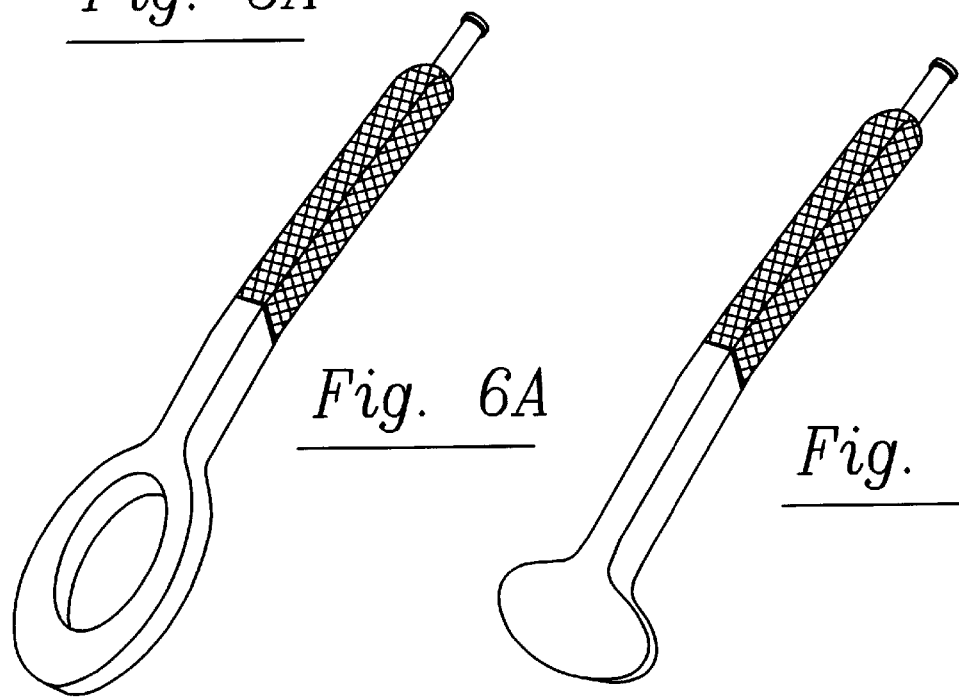
Fig. 6A
Fig. 6B 6,083,003

ELECTROMAGNETICALLY ACTUATED VALVE FOR HYDRAULIC MOTOR VEHICLE BRAKE SYSTEMS

BACKGROUND OF THE INVENTION

1. Field of the Invention

This application claims priority to the provisional patent application of Robert Kwasnik, et. al. for an ORAL VACUUM AND SCRAPER ATTACHMENT filed Oct. 24, 1997. The patent application is based upon and is an improvement of Disclosure Document 381,147 filed in the U.S. Patent and Trademark Office on Oct. 26, 1995. The present invention relates generally to devices utilized to clean the tongue and oral cavity, and more particularly, to oral hygiene devices capable of suctioning and removing matter from the tongue or mouth. Specifically disclosed are various mouthpieces capable of suctioning, scraping and suctioning, or brushing and suctioning, debris and/or foreign matter such as mouth rinse, toothpaste, food particles, volatile sulfur compound producing bacteria, and the like from the tongue and mouth.

2. Description of Related Art

Oral hygiene devices have been in use for years. The traditional toothbrush has been adapted in a number of ways to provide a suction force to remove matter from a mouth of a person as demonstrated by U.S. Pat. Nos. 4,538,631, 5,463,792 and 4,672,953.

One type of prior art device utilizes brushes concentrically placed about a central opening. U.S. Pat. No. 4,538,631 teaches this placement as does U.S. Pat. No. 4,672,953 which also includes a manifold for controllably discharging liquid.

A second type of prior art device is illustrated by U.S. Pat. No. 5,463,792 which teaches the placement of a suction area opposite the bristles of the toothbrush in order to help keep mouth debris out of the bristles.

Other devices have utilized water to assist in the process of oral hygiene including a jet tooth brush (U.S. Pat. No. 3,593,707) and a turbine powered dental treatment apparatus (U.S. Pat. No. 4,808,109).

Further still, aspirator devices of various types are common in the art.

A need exists for an improved oral vacuum and scraper attachment. Furthermore, a need exists for a combination oral hygiene device having a suctioning capacity near an edge of the hand held portion.

A need exists for a combination device having a mouthpiece with a suction area capable of being located in close proximity to an area to be suctioned.

A need exists for an improved oral scraper attachment capable of both scraping and suctioning.

A need exists for an oral vacuum and scraper attachment suitable for home use.

Furthermore, a need exists for a method of scraping and vacuuming a person's mouth which may be performed either at a dentist's office or at a person's home.

A need exists for an improved portable vacuum and scraper attachment.

A need also exists for a vacuum and suction device for oral hygiene configured to be utilized in a person's home.

Additionally, a need exists for an oral hygiene device which may be cleaned easily.

SUMMARY OF THE INVENTION

The present invention recognizes and addresses the foregoing advantages, and others, of prior art construction and methods.

Accordingly, it is an object of the present invention to provide an improved oral vacuum and scraper device that is suitable for use either at a dental office or by a user at home. Suctioning action of the device may be produced either by attachment to suctioning equipment, such as mechanical suctioning equipment as is found in most dentists' offices, or by use of a venturi type suctioning device attached to a sink faucet or other similar source of flowing fluid.

A first advantage of a presently preferred embodiment is the locating of a suction area so that the suction area is in close proximity to a desired suction locale within a person's mouth. Positioning the suction area in this manner may allow a user to position the suction area close to the location to be suctioned.

A second advantage of a presently preferred embodiment is the inclusion of a scraping portion with a suction mechanism.

A third advantage of a presently preferred embodiment is the ability to provide reverse flow to allow water to flow out of the suction area.

Another advantage of the presently preferred embodiment is the ability to control the magnitude of the vacuum drawn into the suction area.

Still, another advantage of the presently preferred embodiment is the inclusion of an aperture which may quickly reduce the force of a vacuum applied to the suction area.

Also in an alternative embodiment, bristles may dislodge foreign matter to encourage the matter to be drawn into the suction area.

Another advantage is the ability to clean the instrument either by suctioning a solution through the suction device or by reversing flow of the venturi device and flushing portions of the oral hygiene device with the fluid which is utilized to create the venturi-effect suction in the venturi device.

Additional objects and advantages of the invention will be set forth in part in the following description, or may be obvious from the description or accompanying drawings, or may be learned through practice of the invention.

The accompanying drawings, which are incorporated in and constitute a part of the specification, illustrate several embodiments of the invention and together with the description serve to explain the principles of the invention.

BRIEF DESCRIPTION OF THE DRAWINGS

FIG. 1 is a perspective view of a first preferred and a second alternatively preferred embodiment of the present invention as viewed from a top angle.

FIG. 2 is perspective view of a first preferred and a second alternatively preferred embodiment of the present invention as viewed from a bottom angle.

FIG. 5 is a perspective view of a third preferred and a fourth alternatively preferred embodiment of the present invention as viewed from a top angle.

FIG. 6 is perspective view of a third preferred and a fourth alternatively preferred embodiment of the present invention as viewed from a bottom angle.

Figure 3:
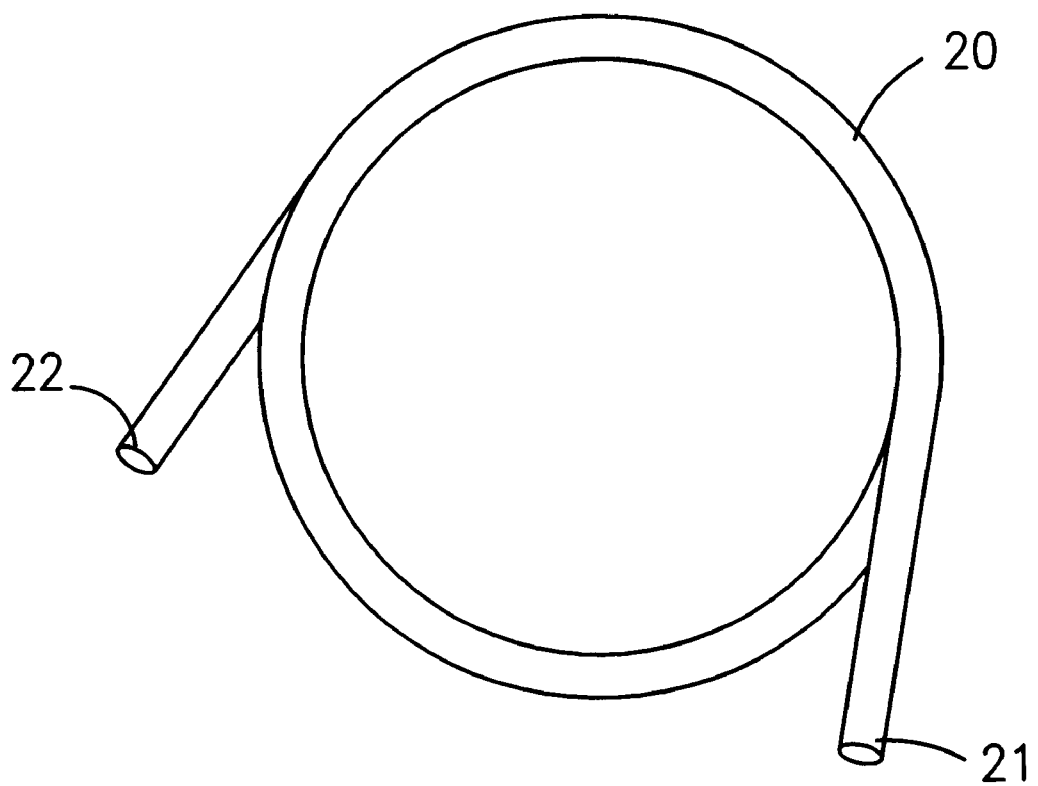
FIG. 3 is a perspective view of a connection device utilized in the presently preferred embodiment of the present invention.

Repeat use of reference numerals in the present specification represent like, similar or analogous parts, features or elements of the present invention throughout several views.

DETAILED DESCRIPTION OF THE PREFERRED EMBODIMENTS

Reference will now be made in detail to the presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield still a further embodiment. Thus, it is intended that the present invention covers such modifications and variations as come within the scope of the appended claims and their equivalents.

The present invention is concerned with an improved oral hygiene device, specifically an oral vacuum and scraper attachment.

Figure 4:
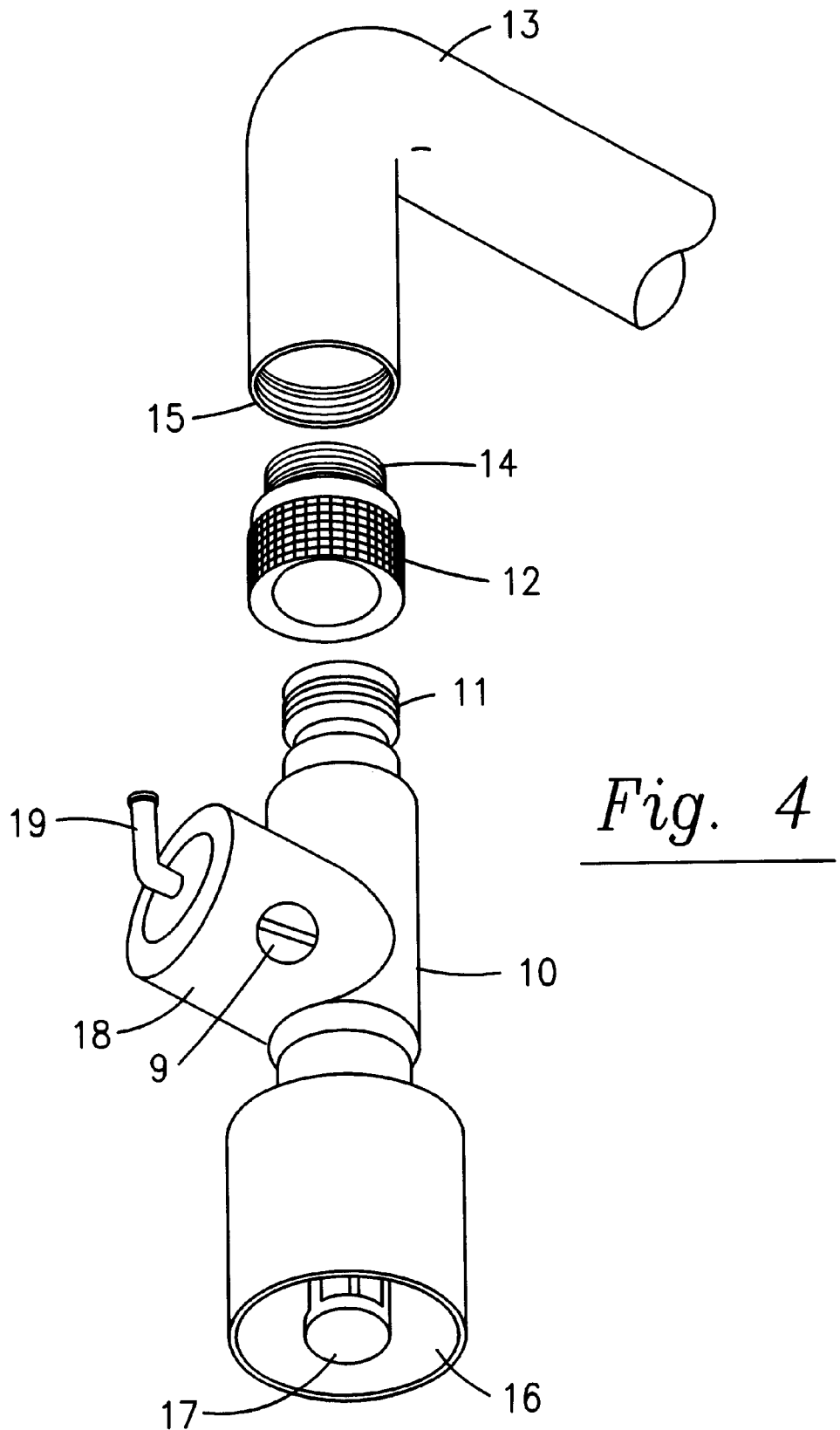
FIG. 4 is an exploded view of a venturi suctioning device of the presently preferred embodiment in the present invention.

Accordingly, FIG. 4 is an exploded view of a suctioning device, a venturi suction device 10. The venturi suctioning device 10 has a well known internal construction. Specifically, a venturi device 10 utilizes a tube with flared ends and a constricted middle portion. When fluid is passed through the tube, the constricted middle causes the pressure to decrease as the velocity of the fluid flow increases. Thus an opening into the constricted portion of the tube will produce suction. The suctioning device is capable of applying a suctioning force at the opening.

In the present design, the faucet connector 12 at a first end may be permanently or semi-permanently attached to the faucet 13 and preferably has the appearance of a common aerator attachment. The venturi device 10 has a quick release type connection in the form of a snap-on fitting 11 which mates (preferably by snap-on or quick release type connection) with a faucet connector 12 at an opposing second end. This device is known in the art and may be manufactured out of any number of materials including metals and plastics. The venturi device 10 need not be separable from a water source by a quick disconnect mechanism, but may be attached by any connection means known in the art. Alternatively, the venturi device 10 may be permanently attached to a water source such as the standard faucet 13 illustrated in FIG. 1, or directly connected to water piping apart from a faucet.

When it is desirable for the venturi device 10 to be removable from the fluid source (illustrated as a standard faucet 13, but not intended to be limited to such), the preferred embodiment utilizes a faucet connector 12 having a male threaded portion 14. The male threaded portion 14 may be received in a female threaded portion 15 of the standard faucet 13 after the aerator of the faucet 13 is removed. Other types of connections between the faucet connector 12 and the faucet 13 may be possible. Other fluid sources might include hoses, nozzles, other than standard faucets, or the like. Additionally, air hoses and valves may be utilized to create a suction through a venturi type device 10 such as the one illustrated in FIG. 4.

Water is utilized in the preferred embodiment as the fluid source. In the presently preferred embodiment, when water is turned on through a faucet 13, it flows through the venturi device 10 and out the lower end 16 into a sink. The venturi device 10 is preferably fitted with a baffle 17 to break up the force of the water flow through the device. This baffle 17 is not required for the venturi device 10 to operate to cause a suction. The baffle 17, when and if installed, may act to reduce the force of the vacuum created by the device.

In a preferred embodiment, attached at the central section of venturi device 10 is an opening through protrusion 18 that has fitting 19 to join to suction hose 20 (illustrated in FIG. 3). The opening is where the suction force is applied. A switch 9 can be activated to divert at least a portion of fluid flow directly from the fluid source (illustrated as a faucet 13) out the connector 19 and through the suction hose 20. This may allow for flushing an area within a mouth by an operator or, alternatively, provide an easy method for cleaning the suction hose 20 and attached mouthpiece 25. The switch 9 may also be installed in a manner to vary the strength of the vacuum force at the suction head by varying the area of the middle constricted portion of the venturi device 10.

FIG. 3 illustrates a connection device, a suction hose 20, utilized in the presently preferred embodiment. Any connection device could be utilized including piping, flexible conduit or the like may be utilized. In the preferred embodiment, the first end 21 of a suction hose 20 is attached to the fitting 19 and a second end 22 of suction hose 20 is attached to a desired mouthpiece 25. The handle end 26 of mouthpiece 25 (illustrated in FIGS. 1, 2, 5 and 6), for instance, would fit into the second end 22 of suction hose 20. Various connection means commonly known in the art may be utilized to join the suction hose 20 to the venturi device 10 and/or to the mouthpiece 25.

In a preferred embodiment, the faucet connector 12 is used to couple the venturi device 10 to the faucet 13 or other similar source of fluid flow. It performs this function by having male threads 14 at the top to attach to most standard faucets 13 and the female component of the snap-on or quick release type coupler at the bottom end into which the male component 11 of the venturi device 10 will be inserted. The apparatus can also be adapted to perform the function of an aerator as well, as by use of baffle 17. Alternatively, if the quick release type coupler is utilized and the venturi device 10 is decoupled from the faucet connecter 12, the faucet connector 12 may remain attached to the faucet 13. In this arrangement, the faucet connecter 12 may function as an aerator.

If the venturi device 10 is made sufficiently compact and provides the aerator function, it may even remain attached to the faucet 13 and operate in the same manner as a faucet aerator when the remaining parts such as suction hose 20 and mouthpiece 25 are not in use and/or are disconnected. Use of the venturi device 10 is optional and the scraper and the vacuum attachment device works equally well when directly connected to a vacuum source, as may be possible in a dentist's or hygienist's office.

Oral hygiene and oral malodor is, or can be, significantly affected by debris such as food particles, volatile sulfur compound producing bacteria, plaque, and the like remaining within the mouth and especially on the tongue. FIGS. 1, 2, 5 and 6 illustrate several alternatively preferred embodiments of the mouthpiece portion of the present invention. This invention is primarily directed towards use in humans, but it will be easily seen that the attachment may be used by veterinarians on other animals. Additionally, while a common method of use is for an individual to use the device to clean his or her own mouth, but this device could be utilized by a person to clean the mouth area of another, as would typically be the case in a dentist's office.

Referring now to FIG. 1, the mouthpieces 25 may be used in connection with suction produced either by mechanical suctioning equipment or a venturi-type suctioning device 10 as described above. The mouthpiece 25 is comprised of a wand portion 28 and a head 27. The wand portion 28 has a proximal end and a distal end. The head 27 is connected to the wand portion 28 at a proximal end of the wand portion 28. The venturi device 10 may be attached to a sink faucet 13 or other source of fluid flow and when the mouthpiece 25 is used on a regular basis, will effectively reduce the presence of debris, volatile sulfur compound producing bacteria, plague, and the like to improve oral hygiene. Of course, better cleaning may be experienced when a user of the present invention accompanies the scraping and suctioning with brushing and/or flossing.

Use of the venturi suctioning device 10 and its intended method with mouthpiece 25 permits home brushing, scraping, and suctioning of the mouth and tongue in a fashion heretofore only easily available in the offices of dentists or dental hygiene professionals. The same mouthpiece provides dental professionals with an improved tool for their work.

A vacuum attachment in the form of a mouthpiece 25 is a key component to this invention, being specially designed to remove debris from the tongue and mouth. The mouthpiece 25 is preferably designed to permit it to reach any part of the mouth, but especially the tongue dorsum where bacteria build-up can be severe. In a presently preferred embodiment, the entire length of the wand portion 28 and head 27, 29, located at a proximal end of the mouthpiece 25, is typically approximately 6.75 inches, but may comfortably range from between about 5 and 8 inches. The wand portion 28 extends from a terminal portion 26 at a distal end of the wand portion 28 to the head 27, 29 and has a hollow channel extending from the proximal end to the distal end, preferably approximately 3/32 inches in diameter to allow the suction through the device from suction hose 20 to be transmitted to suction area 30 in the head 27, 29.

The mouthpiece 25 is preferably constructed from an FDA (Food and Drug Administration) approved grade of polyethylene. Toothbrushes are often constructed out of this same type of material. Any moldable FDA approved material and grade would be an adequate substitute.

The terminal portion 26 can be varied in size and shape to fit a variety of tubing sizes and tubing interlocking devices. The terminal portion 26 connects to the connecting device allowing communication between the connecting device and the mouthpiece 25. Specifically, the terminal portion 26 can be varied to fit into suction devices typically available at dental professionals' offices instead of the illustrated venturi device 10. The portion of the wand 28 adjacent the vacuum tube terminal portion 26 is designed for a comfortable and secure grip. In a presently preferred embodiment, the grip may be rubberized, however it should be apparent to one skilled in the art that it may be made of any material including the material of the wand portion 28 itself.

On the underside of the grip area, in a presently preferred embodiment, is an aperture 31 connected to the hollow channel within the wand portion 28. The aperture 31 is preferably located on an outer surface of the wand 28. This aperture 31 is preferably covered during vacuuming use of the mouthpiece 25. When the aperture 31 is uncovered, air is free to flow through that aperture 31 and substantially reduce the vacuum applied to the suction area 30. The aperture 31 also preferably is a slot ½ inch long and 2/32 inches wide. An alternative embodiment of the aperture is a 3/32 inch diameter circle. The aperture 31 may be fashioned in a number of possible shapes and sizes. Additionally, the aperture 31 need not necessarily be on the underside of the wand 28.

The aperture 31 of the preferred embodiment may function as a vacuum break. The aperture 31 may be utilized as a safety feature as it may prevent any suction mishaps. The aperture 31 may also allow the user to slightly modify the level of suction applied through the suction area 30 of the mouthpiece 25.

In a preferred embodiment, a first portion of the wand portion 28 nearer the proximal end than a second portion of the wand portion 28 form an angle. Preferably, the angle is between the aperture 31 and head 27 and is roughly at the same angle as toothbrush designs and preferably between approximately 5 and 30 degrees. Angles of up to 90 degrees may be useful in certain applications. This bend serves to allow good reach into the back portion of the mouth. The head 27, 29 of the mouthpiece 25 may be designed with some variety and several designs are described separately and are illustrated as alternative embodiments in FIGS. 1, 2, 5 and 6. These alternatively preferred embodiments are provided as examples and are not intended to limit the scope of this invention in any way.

The first head variation 29 illustrated in FIG. 1 and FIG. 2 has an oval shape, much in the configuration of the outer edge of a spoon, with a diameter of approximately one inch. The head 29 has a proximal end, a distal end, a front end, and a back end. Preferably, an outer edge encompasses the proximal end and at least a portion of each of the front and back ends. Alternative diameter dimensions may be utilized so long as the resulting head 27,29 fits comfortably in the mouth. Likewise, the shape of the oval may be varied according to a desired use. In fact, an oval shape is not required at all, but it has been found to be effective both in its construction and utilization.

The head 29 is formed in a loop fashion in the preferred embodiment 28 illustrated in FIG. 1. A hollow portion within the wand portion 28 continues into the perimeter sections of the loop of head 29 and connects with the suction area 30. Therefore, the loop sections are partially hollow so as to connect the suction area 30 to the channel within the wand portion 28 so that fluid may communicate between the suction area 30 and the channel within the wand portion 28. The suction area 30, in the preferred embodiment, is in communication in a similar manner as with the channel within the wand portion 28 as with the connection device 20 and the suction device.

The suction area 30 is preferably located relatively close to an outer edge of the head 29 and on the underside, or bottom surface, of the head 29 beginning near the top portion 32 and running sideways from substantially the front end to substantially the back end with a total semicircular length of approximately ¾ of an inch. A portion of the suction area 30 may approximately parallel a portion of an outer arcuate edge of the head 29. The magnitude of the area chosen the suction area 30 will affect the strength of the vacuum force observed at the suction area 30.

The shape of the suction area 30 may vary as required for a particular use. Additionally, multiple suction areas 30 may be utilized. It is contemplated that the suction area 30 may contain either arcuate and/or linear portions. The width of the suction area 30 in the presently preferred embodiment is approximately 1/16 of an inch but may taper as it approaches the lateral ends. However, the width of the suction area 30 need not be limited to 1/16 of an inch. The suction area 30 is in communication with the hollow channel in the wand portion 28 and is located close to arcuate outer edge of the head 29.

The edge 32 forward of suction area 30 may be raised slightly from the trailing edge 33 behind suction area 30 in a preferred embodiment. This allows raised edge 32 to serve as a scraping portion on a bottom surface which may scrape debris toward and ultimately into the suction area 30 where it can be pulled through the lumen of the wand portion 28 back to the venturi device 10 and down the wastewater drain in the sink. Other scraping portions may be utilized such as teeth, a raised portion, or any other means as known in the art. Furthermore, the raised edge need not be forward of the suction area 30. Additionally, the scraping portion of the suction area 30 need not necessarily contain sharp corners. It is contemplated that many surfaces shown in the illustrated mouthpiece 25 in FIGS. 1, 2, 5 and 6 may have rounded edges, especially the suction area 30.

In a second alternatively preferred embodiment illustrated in FIG. 1 and FIG. 2, the head 27 also has an oval shape. However, unlike head 29, head 27 does not contain a bore in the center of the head 27. The diameter from side to side is approximately one inch, however this head 27 could take any of a number of shapes and sizes.

In the second alternatively preferred embodiment, suction from vacuum hose 20 proceeds through the wand portion 28 to the suction area 30. The suction area 30 is an opening beginning near the top 32 running sideways in either direction with a total arcuate length of approximately 0.75 inches. Multiple suction areas 30 may be utilized, and the suction area 30 may take on a shape as required for the particular application. In a second presently preferred embodiment, the width of this opening is preferably approximately 1/16 inch though the opening may taper as it approaches the lateral sides of the suction area. Again, forward edge 32 may be preferably slightly raised by approximately 1/32 to 1/64 inch from trailing edge 33. This assists in allowing the raised edge 32 to scrape debris back toward and ultimately into the suction area 30 where it can be pulled into suction hose and back through waste drain of the venturi device 10 and eventually down the wastewater drain in the sink.

The third and fourth alternative embodiments 35,36 utilize head designs shown in FIG. 5 and FIG. 6. The third alternative head design is very similar to head 29 shown in FIG. 1 and FIG. 2. The principal distinction is the addition of bristles 37 along the forward edge 32 of head 29. The bristles 37 need not be located forward of the suction area 30, and the bristles 37 might, or might not, completely surround the suction area 30. The bristles 37 may be located proximate to the suction area 30. In a preferred embodiment, bristles 37 are preferably of a length approximately 3/16 to 4/16 inches long. In this embodiment, leading edge 32 need not necessarily be raised, however a scraping device may be utilized in conjunction with bristles 37. The bristles 37 permit brush scrubbing action rather than (or in addition to if edge 32 remains raised) scraping to act as a prelude to suction through the wand portion 28 and suction hose 20 to the venturi device 10.

Similarly, head 36 shown in FIG. 5 and FIG. 6 is analogous to head 27 of FIG. 1 and FIG. 2 except for the addition of short bristles approximately 7/32 inches long lining the forward edge 32. Again, forward edge 32 may be raised to facilitate scraping action, but need not be raised if scrubbing action is sufficient.

It will be understood that alternative designs and slight modifications of the invention are possible and will suggest themselves to those skilled in the art. All such modifications that are contained within the spirit of the specification are intended to come within the scope of this application.

What is claimed is:

1. An oral hygiene device comprising:
    a wand having a channel within said wand, wherein said channel extends from a proximal end to a distal end;
    an aperture on an outer surface of said wand connected to said channel intermediate said proximal and distal end;
    a head having an arcuate forward outer edge, said head connected to said wand, and at least a portion of said head having a hollow portion connected to said channel distal of the aperture in said wand;
    a suction area defined by a substantially arcuate forward edge and a rearward edge, said suction area being located proximate to the forward outer edge of said head, wherein said suction area is connected to said hollow portion of said head and the width of the suction area in the direction perpendicular to the wand is substantially greater than the length of the suction area between the forward and rearward edges defining said area.

2. The oral hygiene device of claim 1 wherein the rearward edge of said suction area is substantially arcuate and parallel to the forward edge.

3. The oral hygiene device of claim 1 wherein said head further comprises bristles located proximate to said suction area.

4. The oral hygiene device of claim 1 wherein a first portion of the wand is nearer to the proximal end than a second portion of the wand, and the first portion of the wand and the second portion of the wand form an angle.

5. The oral hygiene device of claim 4 wherein said angle is between approximately 5 to 30 degrees.

6. The oral hygiene device of claim 1 wherein said head further comprises a scraper portion.

7. The oral hygiene device of claim 6 wherein the scraper portion comprises said forward edge.

8. An oral hygiene mechanism comprising:
    a vacuum attachment having an arcuate head with a suction area proximate an outer edge of the head, said suction area communicating with a hollow channel extending into a terminal portion, said suction area having an arcuate forward edge and a rearward edge, said forward edge raised relative to said rearward edge and forming a scraper portion;
    said arcuate head having a width more than twice its height to fit comfortably in the mouth;
    a connection device attached to the terminal portion of said vacuum attachment providing communication with said hollow channel;
    a suctioning device attached to said connection device providing communication with said connection device and said suction area of said mouthpiece, said suctioning device capable of applying a suction force to said suction area of said mouthpiece.

9. The oral hygiene mechanism of claim 8 wherein said mouthpiece further comprises bristles.

10. The oral hygiene mechanism of claim 8 further comprising an aperture intermediate the head and the suctioning device.

11. The oral hygiene mechanism of claim 8 wherein said suctioning device further comprises a venturi device.

12. The oral hygiene mechanism of claim 11 further comprising a faucet connector attachable to said suctioning device.

13. The oral hygiene mechanism of claim 12 wherein said faucet connector joins a fluid source on a first end and joins said suctioning device on an opposing second end.

14. The oral hygiene mechanism of claim 13 wherein said suctioning device joins said faucet connector with a quick release type connection.

15. The oral hygiene mechanism of claim 12 wherein said suction device further comprises a switch capable of diverting at least a portion of a fluid flow from through the venturi device to through said connection device.

16. A mouth cleaning device comprising:

a mouthpiece having a head and a wand, said head having a proximal end, a distal end, a front end, a back end, an arcuate outer edge encompassing said proximal end, at least a portion of said front end and at least a portion of said back end, and a bottom surface with a suction area, the suction area having an arcuate forward edge raised relative to a substantially parallel rearward edge, said suction area located proximate to said arcuate outer edge of said head and connected to a hollow portion, the suction area extending in a direction from substantially the front end to substantially the back end of the head, the hollow portion communicating with a hollow channel of said wand, and a scraping edge comprising the forward edge of said suction area, said wand having the hollow channel extending from a proximal end to a distal end forming a terminal portion, and an aperture located between a proximal and a distal end of said wand, said aperture communicating with said hollow channel;

a connection device attached to said mouthpiece at the terminal portion, said connection device providing communication with said hollow channel; and a suctioning device attached to said connection device providing communication with said connection device and said suction area of said mouthpiece.

17. The oral hygiene device of claim 16 formed of an FDA approved material.

18. The oral hygiene device of claim 16 wherein said mouthpiece further comprises bristles.

19. The oral hygiene device of claim 16 wherein a first portion of the wand is nearer to the proximal end than a second portion of the wand, and the first portion of the wand and the second portion of the wand form an angle in a range of approximately 5 to approximately 30 degrees.

* * * * *

UNITED STATES PATENT AND TRADEMARK OFFICE
CERTIFICATE OF CORRECTION

PATENT NO. : 6,083,003
DATED : July 4, 2000
INVENTOR(S) : Kwasnik, et al.

It is certified that error appears in the above-identified patent and that said Letters Patent is hereby corrected as shown below:

The title should be -- Oral Vacuum and Scraper Attachment -- instead of "Electromagnetically Actuated Valve For Hydraulic Motor Vehicle Brake Systems."

Signed and Sealed this

Seventh Day of August, 2001

*Attest:*

николаs P. Godici

NICHOLAS P. GODICI
*Attesting Officer*   *Acting Director of the United States Patent and Trademark Office*